(12) United States Patent
Miller et al.

(10) Patent No.: US 8,419,692 B2
(45) Date of Patent: Apr. 16, 2013

(54) INJECTION DEVICE WITH ROTATABLE DOSE SETTING

(75) Inventors: Thomas Dedenroth Miller, Copenhagen O (DK); Steffen Hansen, Hillerod (DK); Niels Christian Egholm Sorensen, Hillerod (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/817,747

(22) Filed: Jun. 17, 2010

(65) Prior Publication Data
US 2010/0318060 A1    Dec. 16, 2010

Related U.S. Application Data

(62) Division of application No. 10/770,586, filed on Feb. 3, 2004, now Pat. No. 7,785, 297.

(60) Provisional application No. 60/446,489, filed on Feb. 11, 2003, provisional application No. 60/485,355, filed on Jul. 7, 2003.

(30) Foreign Application Priority Data

Feb. 4, 2003 (DK) .................................. 2003 00155
Jul. 3, 2003 (DK) .................................. 2003 01011

(51) Int. Cl.
*A61M 5/00* (2006.01)
*A61M 5/30* (2006.01)
(52) U.S. Cl.
USPC ........................................................ 604/211

(58) Field of Classification Search .................. 604/181, 604/187, 207–211, 218
See application file for complete search history.

(56) References Cited

U.S. PATENT DOCUMENTS

| 4,357,971 A | 11/1982 | Friedman |
| 5,424,286 A | 6/1995 | Eng |

(Continued)

FOREIGN PATENT DOCUMENTS

| DE | 42 08 677 A1 | 9/1993 |
| DE | 197 32 909 A1 * | 2/1999 |

(Continued)

OTHER PUBLICATIONS

Office Action and Search Report issued in connection with counterpart Danish Application No. PA 2003 00155, mailed Sep. 15, 2003.

(Continued)

*Primary Examiner* — Matthew F Desanto
(74) *Attorney, Agent, or Firm* — Wesley A. Nicolas; Marc A. Began; Reza Green

(57) ABSTRACT

An injection device comprising a housing and a dose setting mechanism including a dose setting element. Contrary to prior art injection devices, the dose setting element can only be set at a few different dose settings. This is established by forming the dose setting element as a rotatable dish concealed within the housing and having a number of projections projecting outside the boundaries of the housing through a slot in the housing. A dose is set by activating a projection which in addition provides the user with a tactile guidance. Usually one projection is provided for one dose setting limiting the number of doses to be set to the number of projections.

14 Claims, 5 Drawing Sheets

U.S. PATENT DOCUMENTS

| | | | |
|---|---|---|---|
| 5,697,916 | A | 12/1997 | Schraga |
| 5,823,363 | A | 10/1998 | Cassel |
| 6,074,372 | A | 6/2000 | Hansen |
| 6,228,054 | B1 | 5/2001 | Dyarz |
| 6,268,343 | B1 * | 7/2001 | Knudsen et al. ............... 514/4.8 |
| 6,945,961 | B2 | 9/2005 | Miller et al. |
| 2001/0053894 | A1 | 12/2001 | Steenfeldt-Jensen et al. |
| 2002/0088131 | A1 | 7/2002 | Baxa et al. |
| 2005/0165363 | A1 | 7/2005 | Judson et al. |

FOREIGN PATENT DOCUMENTS

| | | |
|---|---|---|
| WO | WO 96/29342 A1 | 9/1996 |
| WO | WO 96/32414 A1 | 10/1996 |
| WO | WO 97/31943 A1 | 9/1997 |
| WO | WO 97/39031 A1 | 10/1997 |
| WO | WO 98/03547 A1 | 1/1998 |
| WO | WO 98/08871 A1 | 3/1998 |
| WO | WO 98/08872 A1 | 3/1998 |
| WO | WO 98/10813 A1 | 3/1998 |
| WO | WO 99/43706 A1 | 9/1999 |
| WO | WO 00/09666 A2 | 2/2000 |
| WO | WO 01/19434 A1 | 3/2001 |
| WO | WO 01/83008 A1 | 11/2001 |
| WO | WO 02/30495 A2 | 4/2002 |
| WO | WO 03008023 * | 1/2003 |

OTHER PUBLICATIONS

Written Opinion and Search Report issued in connection with counterpart PCT Application No. PCT/DK2004/000044, mailed Jun. 21, 2004.

Search Report issued in connection with counterpart PCT Application No. PCT/DK2004/000044, mailed Jul. 19, 2004.

Written Opinion issued in connection with counterpart PCT Application No. PCT/DK2004/000044, mailed Aug. 5, 2005.

* cited by examiner

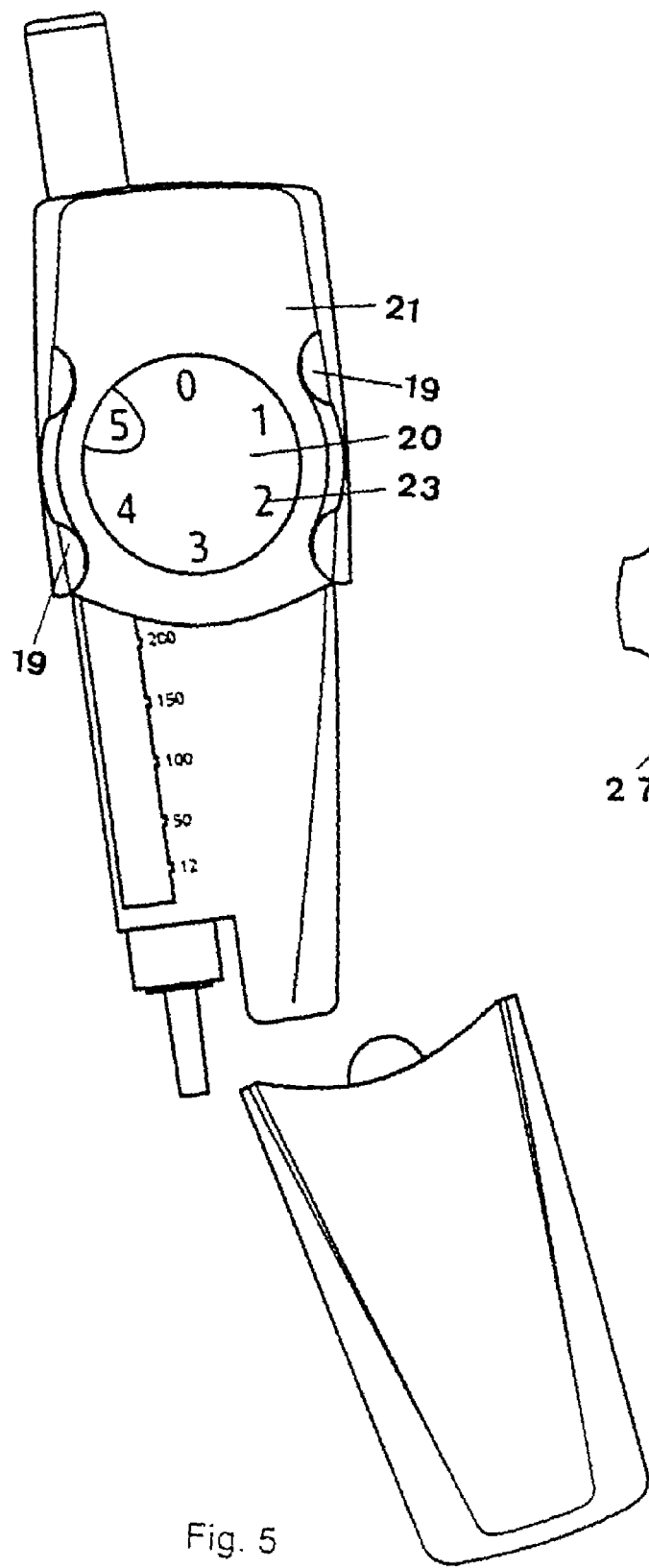
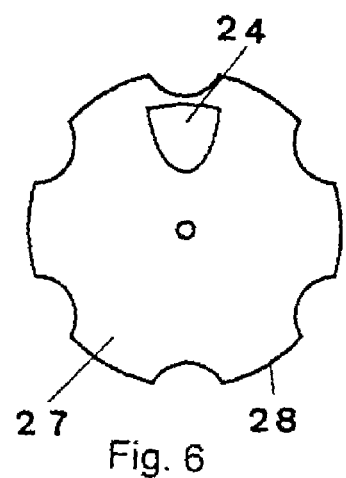
Fig. 5
Fig. 6

INJECTION DEVICE WITH ROTATABLE DOSE SETTING

This application is a divisional application of U.S. application Ser. No. 10/770,586, filed Feb. 3, 2004, which claims priority under 35 U.S.C. 119 of Danish application nos. PA 2003 00155 filed Feb. 4, 2003 and PA 2003 01011 filed Jul. 3, 2003 and of U.S. application Nos. 60/446,489 filed Feb. 11, 2003 and 60/485,355 filed Jul. 7, 2003, the contents of which are fully incorporated herein by reference.

THE TECHNICAL FIELD OF THE INVENTION

The invention relates to injection devices of the kind comprising a housing accommodating a cartridge containing medicine sufficient for a number of dosed injections, the injection device having a dose setting mechanism by which doses can be set from injection to injection by rotating a dose setting element relatively to the housing, the size of the dose being indicated on a scale.

The invention further relates to a method of using such an injection device for the administration of a fluid pharmaceutical formulation comprising a GLP-1 compound or a GLP-2 compound to a patient.

DESCRIPTION OF RELATED ART

A prior art injection device of this kind is disclosed in WO 98/10813. In this known injection device, the scale is formed as a clock dial having a first part secured to the housing and a second part which is rotatable relative to the first part and which second part is coupled to the dose setting mechanism such that the volumetric size of the dose is determined by rotating the second part.

DISCLOSURE OF THE INVENTION

Although a large variety of injection devices are available today, they all have a relatively large number of different dose settings to choose between since it has long been believed that the best treatment of a disease is obtained the more precise a quantum of medicament can be injected.

The injection device known from WO 98/10813 has a scale with approximately 50 to 60 possible dose settings allowing the user to select one of approximately 50 to 60 possible dose settings. This is very beneficial when injecting insulin into the human body in order to obtain a very precise dose and thereby an optimal regulation of the glucose level and thereby of the disease. It is at the same time rather demanding for the user to select the correct dose when the plurality of possible dose settings is that many.

It has however surprisingly shown that for some types of medicaments it is not necessary to inject a very precise dose in order to obtain the optimal treatment of the disease. For some diseases it is adequate to deposit a quantum of the relevant medicament under the skin of patient, which deposit will then graduately be obtained by the body of that patient.

Medicaments suitable for this type of treatment is those who have a biological profile which prohibits overdosing mainly because no, or only harmless side effects occur as a result of overdosing. A medicament comprising a GLP-1 compound is an example on such medicament.

Human GLP-1 is a 37 amino acid residue peptide originating from preproglucagon which is synthesized i.a. in the L-cells in the distal ileum, in the pancreas and in the brain. GLP-1 is an important gut hormone with regulatory function in glucose metabolism and gastrointestinal secretion and metabolism. Processing of preproglucagon to give GLP-1(7-36) -amide, GLP-1(7-37) and GLP-2 occurs mainly in the L-cells. The fragments GLP-1(7-36)-amide and GLP-1(7-37) are both glucose-dependent insulinotropic agents. In the past decades a number of structural analogs of GLP-1 were isolated from the venom of the Gila monster lizards (*Heloderma suspectum* and *Heloderma horridum*). Exendin-4 is a 39 amino acid residue peptide isolated from the venom of *Heloderma horridum*, and this peptide shares 52% homology with GLP-1. Exendin-4 is a potent GLP-1 receptor agonist which has been shown to stimulate insulin release and ensuing lowering of the blood glucose level when injected into dogs. The group of GLP-1(1-37), exendin-4(1-39), certain fragments thereof, analogs thereof and derivatives thereof, (hereinafter designated GLP-1 compounds) are potent insulinotropic agents. Most importantly the group of GLP-1(1-37), exendin-4(1-39), insulinotropic fragments thereof, insulinotropic analogs thereof and insulinotropic derivatives thereof (hereinafter designated GLP-1 compounds) I are also glucose-dependent in their action, i.e. they normalize hyperglycemia but as blood glucose concentration decreases their activity attenuates so that the risk of hypoglycemic events are eliminated or greatly reduced as compared to the conventional treatment with insulin. This lack of severe side effect from overdosing GLP-1 compounds make them very well suited for injecting in only a very few different dose sizes.

A medicament comprising a GLP-2 compound is another example on such medicament. Glucagon-like peptide 2 (GLP-2) is a 33 amino acid residue peptide produced in intestinal L-cells and released following nutrient intake. The GLP-2 peptide is a product of the proglucagon gene. Proglucagon is expressed mainly in the pancreas and the intestine and to some extent in specific neurons located in the brain. The posttranslational processing of proglucagon is however different in pancreas and intestine. In the pancreas proglucagon is processed mainly to Glucagon Related Pancreatic Polypeptide (GRPP), Glucagon and Major Proglucagon Fragment. In contrast to this the processing in the intestine results in Glicentin, Glucagon-Like Peptide 1 (GLP-1) and Glucagon-Like Peptide 2 (GLP-2).

WO 02/30495 discloses an injection device which can inject one preset standard dose size. It is however often the case that the dose size used for a child or juvenile must be lower than the dose size required for a full grown man due to the difference in body mass. It is therefore cumbersome to have an injection device with only one dose size.

It is an object of the present invention to provide an injection device suitable for injecting such a medicament and which injection device only offers the user a limited number of dose settings to chose between.

When only two, three, four or five options are offered to the user, the simplicity in using the injection device is improved. All though the medicaments used in this type of injection devices is the types of medicament which can not be overdosed or which can be injected in very broad intervals without any side effects, it is often necessary to have a number of different dose settings available. This is mainly due to the fact that human beings has different body masses and therefore requires slightly different doses depending on the body mass.

When the dose setting element includes a dish substantially located within the boundaries of the housing and which dish has at least one projection projecting from the dish and extending outside the boundaries of the housing, it is ensured that the user is provided with an improved tactile guidance when setting up a dose such that a user with impaired sight in a save and simple manner can feel tactile feed-back information related to the number of volumetric doses chosen.

A major part of the rotatable dose setting element is encapsulated in the housing and a minor part of the dose setting element such as a projection or the like extends outside the boundaries of the housing. The user is then able to rotate the dose setting element by activating the part accessible from outside the housing. The user can count the number of projections activated and when knowing in what ratio the projections are coordinated with the incremental scale of the specific injection device, the user obtains valuable tactile information regarding the number of dose units chosen.

The projection preferably extends outside the boundaries of the housing through a slot provided in housing. The slot is preferably but not exclusively located in the side surface of the housing When only one full projection is accessible between the upper surface and the lower surface of the slot at the time, it is ensured that a superior tactile guidance is provided since the user can only access one projection of the time. In this embodiment a part of the next and/or the forgoing projection can be visible in the slot, but only one projection at the time is reachable for the user.

With one projection for each volumetric dose unit i.e. the distance between two successive projections equals the setting of one dose unit it is ensured that the counting of the doses set is very easy since the ration between the number of projections and the doses set are 1:1.

The scale markings indicating the set dose on the scale is preferably provided on the partly concealed dish and visible through a window in the housing. However in an embodiment of the injection device according to the invention, the scale markings are provided on a non-rotatable part of the housing and visible through an opening in the rotatable dish. Instead of an opening, the dish could be provided with a pointer pointing out the set dose on a scale on the housing or vice versa. In order to make the device usable for blind people, the scale markings could be made from Braille indications, the window would then have to be an opening through which a blind person can feel the Braille indications.

In further embodiments, the medicine contained in the ampoule is a fluid pharmaceutical formulation comprising a GLP-1 compound. The term "GLP-1 compound", as used herein refers to GLP-1(1-37), exendin-4(1-39), insulinotropic fragments thereof, insulinotropic analogs thereof and insulinotropic derivatives thereof. Insulinotropic fragments of GLP-1(1-37) are insulinotropic peptides for which the entire sequence can be found in the sequence of GLP-1(1-37) and where at least one terminal amino acid has been deleted. Examples of insulinotropic fragments of GLP-1(1-37) are GLP-1(7-37) wherein the amino acid residues in positions 1-6 of GLP-1(1-37) have been deleted, and GLP-1(7-36) where the amino acid residues in position 1-6 and 37 of GLP-1(1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogs of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogs of GLP-1(1-37) is e.g. Met$^8$-GLP-1(7-37) wherein the alanine in position 8 has been replaced by methionine and the amino acid residues in position 1 to 6 have been deleted, and Arg$^{34}$-GLP-1(7-37) wherein the valine in position 34 has been replaced with arginine and the amino acid residues in position 1 to 6 have been deleted. An example of an insulinotropic analog of exendin-4(1-39) is Ser$^2$Asp$^3$-exendin-4(1-39) wherein the amino acid residues in position 2 and 3 have been replaced with serine and aspartic acid, respectively (this particular analog also being known in the art as exendin-3). Insulinotropic derivatives of GLP-1(1-37), exendin-4(1-39) and analogs thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogs thereof are GLP-1(7-36)-amide, Arg$^{34}$, Lys$^{28}$(N$^\epsilon$-(γ-Glu(N$^\alpha$-hexadecanoyl)))-GLP-1(7-37) and Tyr$^{31}$-exendin-4(1-31)-amide. Further examples of GLP-1(1-37), exendin-4(1-39), insulinotropic fragments thereof, insulinotropic analogs thereof and insulinotropic derivatives thereof are described in WO 98/08871, WO 99/43706, U.S. Pat. No. 5,424,286 and WO 00/09666.

In yet further embodiments, the medicine contained in the ampoule is a fluid pharmaceutical formulation comprising a GLP-2 compound. In the present context the GLP-2 compound binds to a GLP-2 receptor, preferably with an affinity constant ($K_D$) or a potency ($EC_{50}$) of below 1 μM, e.g. below 100 nM. The term "GLP-2 compound" encompasses GLP-2 peptides as well as GLP-2 derivatives. Examples of suitable GLP-2 compounds which can be used in the present formulation have been disclosed in e.g. WO 96/29342, WO 97/31943, WO 98/08872, WO 96/32414, WO 97/39031, which are incorporated herein by reference.

The term "GLP-2 peptide" as used herein means any protein comprising the amino acid sequence 1-33 of native human GLP-2 or analogs thereof.

The term "GLP-2" as used herein is intended to include proteins that have the amino acid sequence 1-33 of native human GLP-2. It also includes proteins with a slightly modified amino acid sequence, for instance, a modified N-terminal end including N-terminal amino acid deletions or additions so long as those proteins substantially retain the activity of GLP-2. "GLP-2" within the above definition also includes natural allelic variations that may exist and occur from one individual to another. Also, degree and location of glycosylation or other post-translation modifications may vary depending on the chosen host cells and the nature of the host cellular environment.

The term "derivative" is used in the present text to designate a peptide in which one or more of the amino acid residues have been chemically modified, e.g. by alkylation, acylation, ester formation or amide formation.

The term "a GLP-2 derivative" is used in the present text to designate a derivative of a GLP-2 peptide. In one embodiment the GLP-2 derivative according to the present invention has GLP-2 activity as measured by the ability to bind a GLP-2 receptor (GLP-2R) and/or exert a trophic effects on the small or large intestine. In one embodiment the GLP-2 receptor is selected from the list consisting of rat GLP-2R, mouse GLP-2R and human GLP-2R.

The term "lipophilic substituent" is characterised by comprising 4-40 carbon atoms and having a solubility in water at 20° C. in the range from about 0.1 mg/100 ml water to about 250 mg/100 ml water, such as in the range from about 0.3 mg/100 ml water to about 75 mg/100 ml water. For instance, octanoic acid (C8) has a solubility in water at 20° C. of 68 mg/100 ml, decanoic acid (C10) has a solubility in water at 20° C. of 15 mg/100 ml, and octadecanoic acid (C18) has a solubility in water at 20° C. of 0.3 mg/100 ml.

Candidate GLP-2 compounds, which may be used according to the present invention may be, for instance, the GLP-2 analogs as described in WO 96/32414, WO 97/39031, WO 98/03547, the GLP-2 derivatives as described in WO 96/29342, WO 97/31943, WO 98/08872, incorporated herein by reference.

In one embodiment of the invention the GLP-2 compound is a GLP-2 derivative.

In one embodiment of the invention the GLP-2 compound is a GLP-2 peptide.

In one embodiment of the invention the GLP-2 peptide is selected from the list consisting of:
A2G-GLP-2(1-33); K30R-GLP-2(1-33); S5K-GLP-2(1-33); S7K-GLP-2(1-33); D8K-GLP-2(1-33); E9K-GLP-2(1-33); M10K-GLP-2(1-33); N11K-GLP-2(1-33); T12K-GLP-2(1-33); I13K-GLP-2(1-33); L14K-GLP-2(1-33); D15K-GLP-2(1-33); N16K-GLP-2(1-33); L17K-GLP-2(1-33); A18K-GLP-2(1-33); D21K-GLP-2(1-33); N24K-GLP-2(1-33); Q28K-GLP-2(1-33); S5K/K30R-GLP-2(1-33); S7K/K30R-GLP-2(1-33); D8K/K30R-GLP-2(1-33); E9K/K30R-GLP-2(1-33); M10K/K30R-GLP-2(1-33); N11K/K30R-GLP-2(1-33); T12K/K30R-GLP-2(1-33); I13K/K30R-GLP-2(1-33); L14K/K30R-GLP-2(1-33); D15K/K30R-GLP-2(1-33); N16K/K30R-GLP-2(1-33); L17K/K30R-GLP-2(1-33); A18K/K30R-GLP-2(1-33); D21K/K30R-GLP-2(1-33); N24K/K30R-GLP-2(1-33); Q28K/K30R-GLP-2(1-33); K30R/D33K-GLP-2(1-33); D3E/K30R/D33E-GLP-2(1-33); D3E/S5K/K30R/D33E-GLP-2(1-33); D3E/S7K/K30R/D33E-GLP-2(1-33); D3E/D8K/K30R/D33E-GLP-2(1-33); D3E/E9K/K30R/D33E-GLP-2(1-33); D3E/M10K/K30R/D33E-GLP-2(1-33); D3E/N11K/K30R/D33E-GLP-2(1-33); D3E/T12K/K30R/D33E-GLP-2(1-33); D3E/I13K/K30R/D33E-GLP-2(1-33); D3E/L14K/K30R/D33E-GLP-2(1-33); D3E/D15K/K30R/D33E-GLP-2(1-33); D3E/N16K/K30R/D33E-GLP-2(1-33); D3E/L17K/K30R/D33E-GLP-2(1-33); D3E/A18K/K30R/D33E-GLP-2(1-33); D3E/D21K/K30R/D33E-GLP-2(1-33); D3E/N24K/K30R/D33E-GLP-2(1-33); and D3E/Q28K/K30R/D33E-GLP-2(1-33).

In one embodiment of the invention the GLP-2 compound is A2G-GLP-2(1-33).

In one embodiment of the invention the GLP-2 derivative only has one lipophilic substituent attached to the GLP-2 peptide.

In one embodiment of the invention the lipophilic substituent comprises from 4 to 40 carbon atoms.

In one embodiment of the invention the lipophilic substituent comprises from 8 to 25 carbon atoms.

In one embodiment of the invention the lipophilic substituent comprises from 12 to 20 carbon atoms.

In one embodiment of the invention the lipophilic substituent is attached to an amino acid residue in such a way that a carboxyl group of the lipophilic substituent forms an amide bond with an amino group of the amino acid residue.

In one embodiment of the invention the lipophilic substituent is attached to a Lys residue.

In one embodiment of the invention the lipophilic substituent is attached to an amino acid residue in such a way that an amino group of the lipophilic substituent forms an amide bond with a carboxyl group of the amino acid residue.

In one embodiment of the invention the lipophilic substituent is attached to the GLP-2 peptide by means of a spacer.

In one embodiment of the invention the spacer is selected from the list consisting of β-alanine, gamma-aminobutyric acid (GABA), γ-glutamic acid, Lys, Asp, Glu, a dipeptide containing Asp, a dipeptide containing Glu, or a dipeptide containing Lys. In one embodiment of the invention the spacer is β-alanine. In one embodiment of the invention the spacer is gamma-aminobutyric acid (GABA). In one embodiment of the invention the spacer is γ-glutamic acid.

In one embodiment of the invention a carboxyl group of the parent GLP-2 peptide forms an amide bond with an amino group of a spacer, and the carboxyl group of the amino acid or dipeptide spacer forms an amide bond with an amino group of the lipophilic substituent.

In one embodiment of the invention an amino group of the parent GLP-2 peptide forms an amide bond with a carboxylic group of a spacer, and an amino group of the spacer forms an amide bond with a carboxyl group of the lipophilic substituent.

In one embodiment of the invention the lipophilic substituent is an straight-chain or branched alkyl group. In one embodiment of the invention the lipophilic substituent is the acyl group of a straight-chain or branched fatty acid.

In one embodiment of the invention the lipophilic substituent is an acyl group of a straight-chain or branched alkane α,ω-dicarboxylic acid.

In one embodiment of the invention the GLP-2 derivative has one lipophilic substituent. In one embodiment of the invention the GLP-2 derivative has two lipophilic substituents. In one embodiment of the invention the GLP-2 derivative has three lipophilic substituents. In one embodiment of the invention the GLP-2 derivative has four lipophilic substituents.

In one embodiment of the invention the GLP-2 derivative is selected from the group consisting of
S5K(3-(hexadecanoylamino)propionyl)-GLP-2(1-33);
S7K(3-(hexadecanoylamino)propionyl)-GLP-2(1-33);
D8K(3-(hexadecanoylamino)propionyl)-GLP-2(1-33);
E9K(3-(hexadecanoylamino)propionyl)-GLP-2(1-33);
M10K(3-(hexadecanoylamino)propionyl)-GLP-2(1-33);
N11K(3-(hexadecanoylamino)propionyl)-GLP-2(1-33);
T12K(3-(hexadecanoylamino)propionyl)-GLP-2(1-33);
I13K(3-(hexadecanoylamino)propionyl)-GLP-2(1-33);
L14K(3-(hexadecanoylamino)propionyl)-GLP-2(1-33);
D15K(3-(hexadecanoylamino)propionyl)-GLP-2(1-33);
N16K(3-(hexadecanoylamino)propionyl)-GLP-2(1-33);
L17K(3-(octanoylamino)propionyl)-GLP-2(1-33);
L17K(3-(nonanoylamino)propionyl)-GLP-2(1-33);
L17K(3-(decanoylamino)propionyl)-GLP-2(1-33);
L17K(3-(undecanoylamino)propionyl)-GLP-2(1-33);
L17K(3-(dodecanoylamino)propionyl)-GLP-2(1-33);
L17K(3-(tridecanoylamino)propionyl)-GLP-2(1-33);
L17K(3-(tetradecanoylamino)propionyl)-GLP-2(1-33);
L17K(3-(pentadecanoylamino)propionyl)-GLP-2(1-33);
L17K(3-(hexadecanoylamino)propionyl)-GLP-2(1-33);
L17K(3-(heptadecanoylamino)propionyl)-GLP-2(1-33);
L17K(3-(octadecanoylamino)propionyl)-GLP-2(1-33);
L17K(3-(nonadecanoylamino)propionyl)-GLP-2(1-33);
L17K(3-(eicosanoylamino)propionyl)-GLP-2(1-33);
L17K((S)-4-carboxy-4-(octanoylamino)butanoyl)-GLP-2(1-33);
L17K((S)-4-carboxy-4-(nonanoylamino)butanoyl)-GLP-2(1-33);
L17K((S)-4-carboxy-4-(decanoylamino)butanoyl)-GLP-2(1-33);
L17K((S)-4-carboxy-4-(undecanoylamino)butanoyl)-GLP-2(1-33);

L17K((S)-4-carboxy-4-(dodecanoylamino)butanoyl)-GLP-2(1-33);
L17K((S)-4-carboxy-4-(tridecanoylamino)butanoyl)-GLP-2(1-33);
L17K((S)-4-carboxy-4-(tetradecanoylamino)butanoyl)-GLP-2(1-33);
L17K((S)-4-carboxy-4-(pentadecanoylamino)butanoyl)-GLP-2(1-33);
L17K((S)-4-carboxy-4-(hexadecanoylamino)butanoyl)-GLP-2(1-33);
L17K((S)-4-carboxy-4-(heptadecanoylamino)butanoyl)-GLP-2(1-33);
L17K((S)-4-carboxy-4-(octadecanoylamino)butanoyl)-GLP-2(1-33);
L17K((S)-4-carboxy-4-(nonadecanoylamino)butanoyl)-GLP-2(1-33);
L17K((S)-4-carboxy-4-(eicosanoylamino)butanoyl)-GLP-2(1-33);
L17K(4-(octanoylamino)butanoyl)-GLP-2(1-33);
L17K(4-(nonanoylamino)butanoyl)-GLP-2(1-33);
L17K(4-(decanoylamino)butanoyl)-GLP-2(1-33);
L17K(4-(undecanoylamino)butanoyl)-GLP-2(1-33);
L17K(4-(dodecanoylamino)butanoyl)-GLP-2(1-33);
L17K(4-(tridecanoylamino)butanoyl)-GLP-2(1-33);
L17K(4-(tetradecanoylamino)butanoyl)-GLP-2(1-33);
L17K(4-(pentadecanoylamino)butanoyl)-GLP-2(1-33);
L17K(4-(hexadecanoylamino)butanoyl)-GLP-2(1-33);
L17K(4-(heptadecanoylamino)butanoyl)-GLP-2(1-33);
L17K(4-(octadecanoylamino)butanoyl)-GLP-2(1-33);
L17K(4-(nonadecanoylamino)butanoyl)-GLP-2(1-33);
L17K(4-(eicosanoylamino)butanoyl)-GLP-2(1-33);
A18K(3-(hexadecanoylamino)propionyl)-GLP-2(1-33);
D21K(3-(hexadecanoylamino)propionyl)-GLP-2(1-33);
N24K(3-(hexadecanoylamino)propionyl)-GLP-2(1-33);
Q28K(3-(hexadecanoylamino)propionyl)-GLP-2(1-33);
S5K(3-(hexadecanoylamino)propionyl)/K30R-GLP-2(1-33);
S7K(3-(hexadecanoylamino)propionyl)/K30R-GLP-2(1-33);
D8K(3-(hexadecanoylamino)propionyl)/K30R-GLP-2(1-33);
E9K(3-(hexadecanoylamino)propionyl)/K30R-GLP-2(1-33);
M10K(3-(hexadecanoylamino)propionyl)/K30R-GLP-2(1-33);
N11K(3-(hexadecanoylamino)propionyl)/K30R-GLP-2(1-33);
T12K(3-(hexadecanoylamino)propionyl)/K30R-GLP-2(1-33);
I13K(3-(hexadecanoylamino)propionyl)/K30R-GLP-2(1-33);
L14K(3-(hexadecanoylamino)propionyl)/K30R-GLP-2(1-33);
D15K(3-(hexadecanoylamino)propionyl)/K30R-GLP-2(1-33);
N16K(3-(hexadecanoylamino)propionyl)/K30R-GLP-2(1-33);
L17K(3-(octanoylamino)propionyl)/K30R-GLP-2(1-33);
L17K(3-(nonanoylamino)propionyl)/K30R-GLP-2(1-33);
L17K(3-(decanoylamino)propionyl)/K30R-GLP-2(1-33);
L17K(3-(undecanoylamino)propionyl)/K30R-GLP-2(1-33);
L17K(3-(dodecanoylamino)propionyl)/K30R-GLP-2(1-33);
L17K(3-(tridecanoylamino)propionyl)/K30R-GLP-2(1-33);
L17K(3-(tetradecanoylamino)propionyl)/K30R-GLP-2(1-33);
L17K(3-(pentadecanoylamino)propionyl)/K30R-GLP-2(1-33);
L17K(3-(hexadecanoylamino)propionyl)/K30R-GLP-2(1-33);
L17K(3-(heptadecanoylamino)propionyl)/K30R-GLP-2(1-33);
L17K(3-(octadecanoylamino)propionyl)/K30R-GLP-2(1-33);
L17K(3-(nonadecanoylamino)propionyl)/K30R-GLP-2(1-33);
L17K(3-(eicosanoylamino)propionyl)/K30R-GLP-2(1-33);
L17K((S)-4-carboxy-4-(octanoylamino)butanoyl)/K30R-GLP-2(1-33);
L17K((S)-4-carboxy-4-(nonanoylamino)butanoyl)/K30R-GLP-2(1-33);
L17K((S)-4-carboxy-4-(decanoylamino)butanoyl)/K30R-GLP-2(1-33);
L17K((S)-4-carboxy-4-(undecanoylamino)butanoyl)/K30R-GLP-2(1-33);
L17K((S)-4-carboxy-4-(dodecanoylamino)butanoyl)/K30R-GLP-2(1-33);
L17K((S)-4-carboxy-4-(tridecanoylamino)butanoyl)/K30R-GLP-2(1-33);
L17K((S)-4-carboxy-4-(tetradecanoylamino)butanoyl)/K30R-GLP-2(1-33);
L17K((S)-4-carboxy-4-(pentadecanoylamino)butanoyl)/K30R-GLP-2(1-33);
L17K((S)-4-carboxy-4-(hexadecanoylamino)butanoyl)/K30R-GLP-2(1-33);
L17K((S)-4-carboxy-4-(heptadecanoylamino)butanoyl)/K30R-GLP-2(1-33);
L17K((S)-4-carboxy-4-(octadecanoylamino)butanoyl)/K30R-GLP-2(1-33);
L17K((S)-4-carboxy-4-(nonadecanoylamino)butanoyl)/K30R-GLP-2(1-33);
L17K((S)-4-carboxy-4-(eicosanoylamino)butanoyl)/K30R-GLP-2(1-33);
L17K(4-(octanoylamino)butanoyl)/K30R-GLP-2(1-33);
L17K(4-(nonanoylamino)butanoyl)/K30R-GLP-2(1-33);
L17K(4-(decanoylamino)butanoyl)/K30R-GLP-2(1-33);
L17K(4-(undecanoylamino)butanoyl)/K30R-GLP-2(1-33);
L17K(4-(dodecanoylamino)butanoyl)/K30R-GLP-2(1-33);
L17K(4-(tridecanoylamino)butanoyl)/K30R-GLP-2(1-33);
L17K(4-(tetradecanoylamino)butanoyl)/K30R-GLP-2(1-33);
L17K(4-(pentadecanoylamino)butanoyl)/K30R-GLP-2(1-33);
L17K(4-(hexadecanoylamino)butanoyl)/K30R-GLP-2(1-33);
L17K(4-(heptadecanoylamino)butanoyl)/K30R-GLP-2(1-33);
L17K(4-(octadecanoylamino)butanoyl)/K30R-GLP-2(1-33);
L17K(4-(nonadecanoylamino)butanoyl)/K30R-GLP-2(1-33);
L17K(4-(eicosanoylamino)butanoyl)/K30R-GLP-2(1-33);
A18K(3-(hexadecanoylamino)propionyl)/K30R-GLP-2(1-33);
D21K(3-(hexadecanoylamino)propionyl)/K30R-GLP-2(1-33);
N24K(3-(hexadecanoylamino)propionyl)/K30R-GLP-2(1-33);
Q28K(3-(hexadecanoylamino)propionyl)/K30R-GLP-2(1-33);
D3E/S5K(3-(hexadecanoylamino)propionyl)/K30R/D33E-GLP-2(1-33);
D3E/S7K(3-(hexadecanoylamino)propionyl)/K30R/D33E-GLP-2(1-33);

D3E/D8K(3-(hexadecanoylamino)propionyl)/K30R/D33E-GLP-2(1-33);
D3E/E9K(3-(hexadecanoylamino)propionyl)/K30R/D33E-GLP-2(1-33);
D3E/M10K(3-(hexadecanoylamino)propionyl)/K30R/D33E-GLP-2(1-33);
D3E/N11K(3-(hexadecanoylamino)propionyl)/K30R/D33E-GLP-2(1-33);
D3E/T12K(3-(hexadecanoylamino)propionyl)/K30R/D33E-GLP-2(1-33);
D3E/I13K(3-(hexadecanoylamino)propionyl)/K30R/D33E-GLP-2(1-33);
D3E/L14K(3-(hexadecanoylamino)propionyl)/K30R/D33E-GLP-2(1-33);
D3E/D15K(3-(hexadecanoylamino)propionyl)/K30R/D33E-GLP-2(1-33);
D3E/N16K(3-(hexadecanoylamino)propionyl)/K30R/D33E-GLP-2(1-33);
D3E/L17K(3-(octanoylamino)propionyl)/K30R/D33E-GLP-2(1-33);
D3E/L17K(3-(nonanoylamino)propionyl)/K30R/D33E-GLP-2(1-33);
D3E/L17K(3-(decanoylamino)propionyl)/K30R/D33E-GLP-2(1-33);
D3E/L17K(3-(undecanoylamino)propionyl)/K30R/D33E-GLP-2(1-33);
D3E/L17K(3-(dodecanoylamino)propionyl)/K30R/D33E-GLP-2(1-33);
D3E/L17K(3-(tridecanoylamino)propionyl)/K30R/D33E-GLP-2(1-33);
D3E/L17K(3-(tetradecanoylamino)propionyl)/K30R/D33E-GLP-2(1-33);
D3E/L17K(3-(pentadecanoylamino)propionyl)/K30R/D33E-GLP-2(1-33);
D3E/L17K(3-(hexadecanoylamino)propionyl)/K30R/D33E-GLP-2(1-33);
D3E/L17K(3-(heptadecanoylamino)propionyl)/K30R/D33E-GLP-2(1-33);
D3E/L17K(3-(octadecanoylamino)propionyl)/K30R/D33E-GLP-2(1-33);
D3E/L17K(3-(nonadecanoylamino)propionyl)/K30R/D33E-GLP-2(1-33);
D3E/L17K(3-(eicosanoylamino)propionyl)/K30R/D33E-GLP-2(1-33);
D3E/L17K((S)-4-carboxy-4-(octanoylamino)butanoyl)/K30R/D33E-GLP-2(1-33);
D3E/L17K((S)-4-carboxy-4-(nonanoylamino)butanoyl)/K30R/D33E-GLP-2(1-33);
D3E/L17K((S)-4-carboxy-4-(decanoylamino)butanoyl)/K30R/D33E-GLP-2(1-33);
D3E/L17K((S)-4-carboxy-4-(undecanoylamino)butanoyl)/K30R/D33E-GLP-2(1-33);
D3E/L17K((S)-4-carboxy-4-(dodecanoylamino)butanoyl)/K30R/D33E-GLP-2(1-33);
D3E/L17K((S)-4-carboxy-4-(tridecanoylamino)butanoyl)/K30R/D33E-GLP-2(1-33);
D3E/L17K((S)-4-carboxy-4-(tetradecanoylamino)butanoyl)/K30R/D33E-GLP-2(1-33);
D3E/L17K((S)-4-carboxy-4-(pentadecanoylamino)butanoyl)/K30R/D33E-GLP-2(1-33);
D3E/L17K((S)-4-carboxy-4-(hexadecanoylamino)butanoyl)/K30R/D33E-GLP-2(1-33);
D3E/L17K((S)-4-carboxy-4-(heptadecanoylamino)butanoyl)/K30R/D33E-GLP-2(1-33);
D3E/L17K((S)-4-carboxy-4-(octadecanoylamino)butanoyl)/K30R/D33E-GLP-2(1-33);
D3E/L17K((S)-4-carboxy-4-(nonadecanoylamino)butanoyl)/K30R/D33E-GLP-2(1-33);
D3E/L17K((S)-4-carboxy-4-(eicosanoylamino)butanoyl)/K30R/D33E-GLP-2(1-33);
D3E/L17K(4-(octanoylamino)butanoyl)/K30R/D33E-GLP-2(1-33);
D3E/L17K(4-(nonanoylamino)butanoyl)/K30R/D33E-GLP-2(1-33);
D3E/L17K(4-(decanoylamino)butanoyl)/K30R/D33E-GLP-2(1-33);
D3E/L17K(4-(undecanoylamino)butanoyl)/K30R/D33E-GLP-2(1-33);
D3E/L17K(4-(dodecanoylamino)butanoyl)/K30R/D33E-GLP-2(1-33);
D3E/L17K(4-(tridecanoylamino)butanoyl)/K30R/D33E-GLP-2(1-33);
D3E/L17K(4-(tetradecanoylamino)butanoyl)/K30R/D33E-GLP-2(1-33);
D3E/L17K(4-(pentadecanoylamino)butanoyl)/K30R/D33E-GLP-2(1-33);
D3E/L17K(4-(hexadecanoylamino)butanoyl)/K30R/D33E-GLP-2(1-33);
D3E/L17K(4-(heptadecanoylamino)butanoyl)/K30R/D33E-GLP-2(1-33);
D3E/L17K(4-(octadecanoylamino)butanoyl)/K30R/D33E-GLP-2(1-33);
D3E/L17K(4-(nonadecanoylamino)butanoyl)/K30R/D33E-GLP-2(1-33);
D3E/L17K(4-(eicosanoylamino)butanoyl)/K30R/D33E-GLP-2(1-33);
D3E/A18K(3-(hexadecanoylamino)propionyl)/K30R/D33E-GLP-2(1-33);
D3E/D21K(3-(hexadecanoylamino)propionyl)/K30R/D33E-GLP-2(1-33);
D3E/N24K(3-(hexadecanoylamino)propionyl)/K30R/D33E-GLP-2(1-33); and
D3E/Q28K(3-(hexadecanoylamino)propionyl)/K30R/D33E-GLP-2(1-33).

It is also the object of the present invention to provide a method of using an injection device having up to five different dose sizes for the administration of a fluid pharmaceutical formulation comprising a GLP-1 compound or a GLP-2 compound to a patient. A method that is very simple to use for patients exercising self-injection.

Such a method comprises the steps of connecting a pen needle to the injection device, rotating the dose setting element to select one of the up to five available dose sizes, inserting the pen needle into the patient and injecting the set dose of a fluid pharmaceutical formulation comprising GLP-1 compound or GLP-2 compound, and removing the pen needle from the patient after completing the injection.

Instead of having one injection device with a plurality of different dose sizes it is within the concept of the present invention to have a plurality of substantial identical injection devices that only differs from each other in having a different dose size.

A system comprising a plurality of substantially identical injection devices having different dose sizes is further provided, which dose sizes is fixed and predetermined for each injection device.

Such a system would comprise between 2 to 5 substantially identical injection devices. Each of the 2 to 5 injection devices would have a different dose size such that 2 to 5 different dose sizes are available.

The doctor responsible for the treatment of a patient would prescribe the one injection device taken from the plurality that has the dose size which best accommodates the individual patient.

In this way only one dose size option would be offered to the user all though the system as such would provide the doctor with several options such that the doctor by determining the body mass and condition of the individual patient can select the injection device most suited for the individual patient from the plurality of injection devices. The simplicity for the user only having to set one predetermined dose size is remarkable.

The dose size of each injection device can be determined by the volumetric size of the dose. This could be realized by incorporating a stop member in the injection device e.g. a mechanical stop determining the dose size. This would mean that the plurality of injection devices in the system would have to be mechanical different, but only in features relating to the dose size. Besides this the injection devices in the system is identical.

Alternatively all the injection devices in the system could be mechanical identical but contain the medicament in different concentrations. In this way the same volumetric dose would be injected each time but in different concentrations depending on the chosen injection device.

The medicine contained in the ampoule is preferably either a GLP-1 compound or a GLP-2 compound. The GLP-1 and GLP-2 compounds referred to could be the types defined herein; of course, they need not be so limited.

It is also the object to provide a method of using a system of injection device. According to one embodiment, this method preferably the doctor would select the injection device from the plurality of injection devices that best accommodates the individual patients' needs and physics where after the patient would inject the predetermined dose size by themselves.

The injection device used can either be a disposable or a durable injection device. Disposable injection devices have a reservoir permanently fixed within the housing of the device. When the reservoir, which usually consist of a glass ampoule is empty the entire device is simply disposed of. Durable injection devices have a replaceable ampoule, which, when empty, is replaced by a new, prefilled ampoule.

BRIEF DESCRIPTION OF THE DRAWINGS

The invention will be explained more fully below in connection with a preferred embodiment and with reference to the drawings in which:

FIG. 5 shows an embodiment of the injection device according to the invention.

FIG. 6 shows a front view of the rotatable disc according to an embodiment of the invention.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Figure 1:
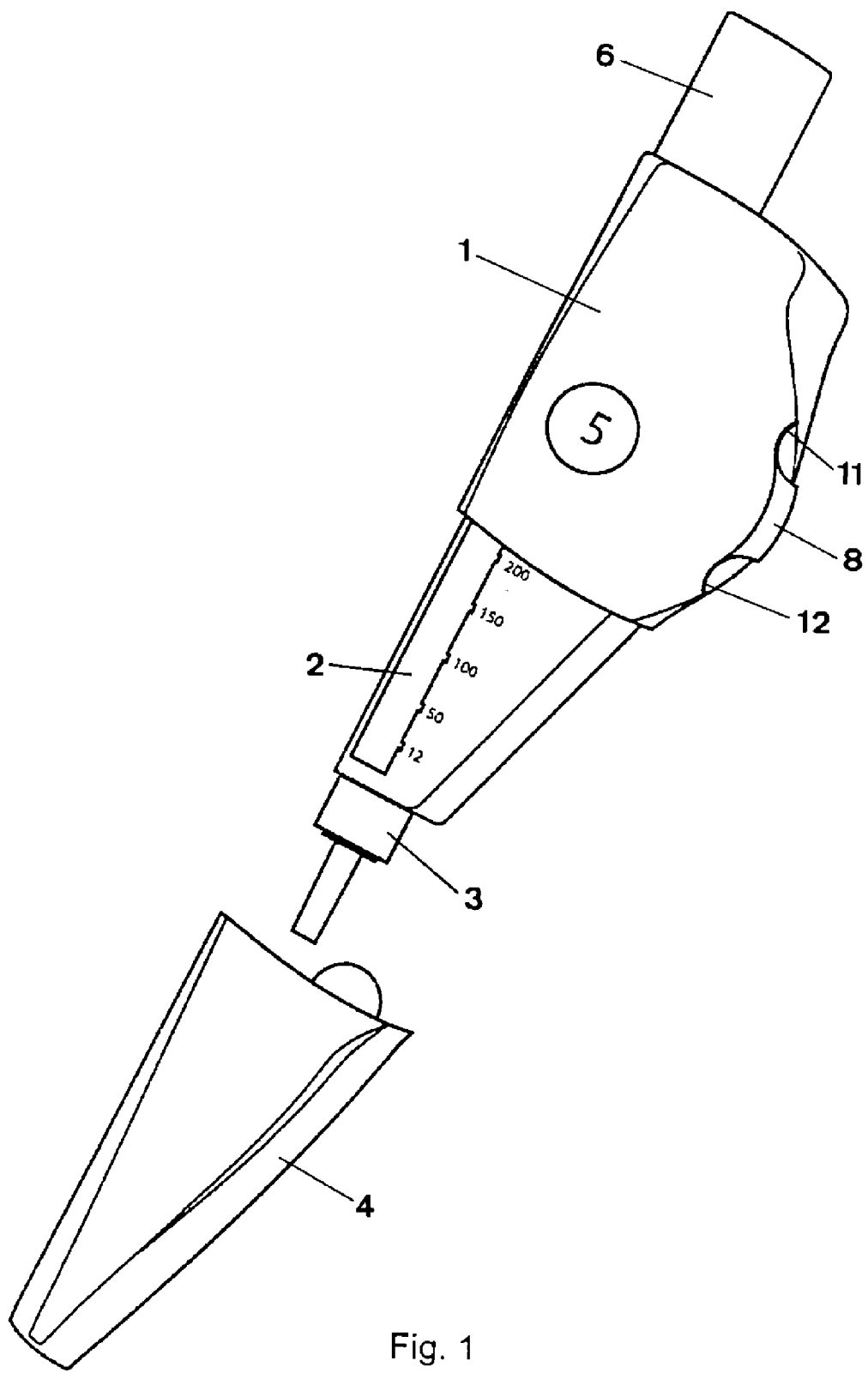
FIG. 1 shows the injection device according to the invention.
Figure 2:
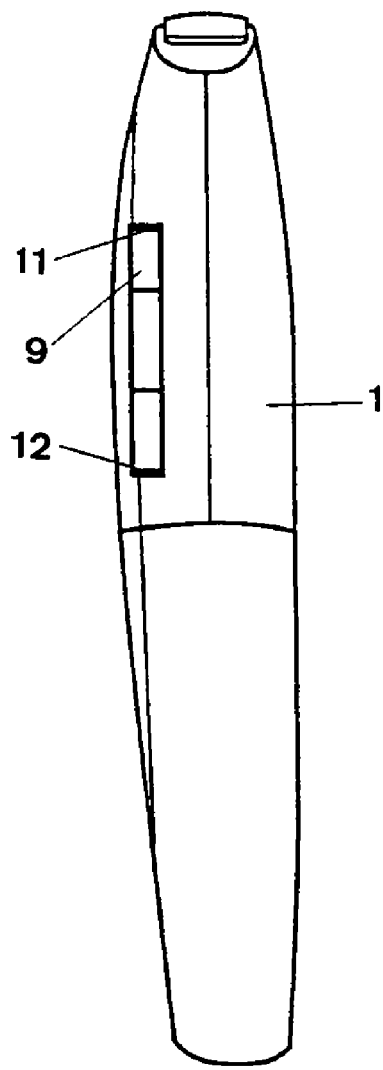
FIG. 2 shows a side view of the injection device in FIG. 1.

Initially it may be convenient to define that the term "distal end" of the housing 1 is meant to refer to the end carrying the injection needle 3, whereas the term "proximal end" is meant to refer to the opposite end carrying the injection button 6.

In FIGS. 1 to 4 is shown a syringe which due to the use of a bendable piston rod are made shorter than an ordinary pen shaped syringe. The pen comprises a housing 1 containing a dose setting mechanism and accommodating an ampoule 2 with medicine to be apportioned. An injection needle 3 is mounted on the distal end of the syringe. The end of the syringe carrying the injection needle 3 may be covered by a protection cap 4 when not in use.

The syringe has a dose setting mechanism which in addition to the dose setting element 5 also comprises an injection button 6. The dose setting element 5 is operational coupled to the dose setting mechanism such that the injection button 6 is elevated from the proximal end of the housing 1 when the dose setting element 5 is rotated to set a dose. The injection button 6 is pressed home to abutment with the housing 1 to inject the set dose as described in details in U.S. Pat. No. 6,074,372, the content of which is hereby incorporated by reference. The dose setting mechanism used preferably comprises a preassembled dose unit as described in details in WO 01/83008, the content of which is hereby incorporated by reference.

Figure 3:
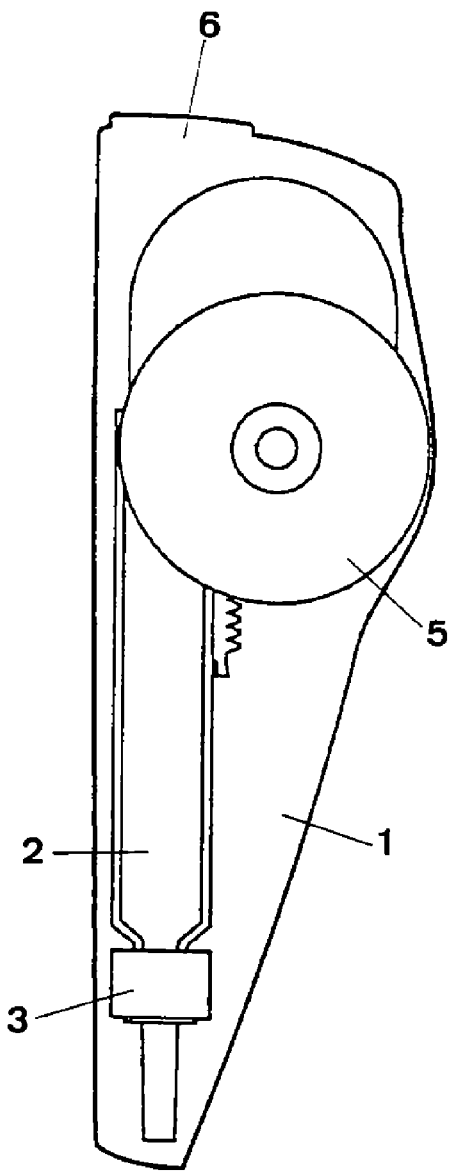
FIG. 3 shows a cross sectional front view of the injection device in FIG. 1.
Figure 4:
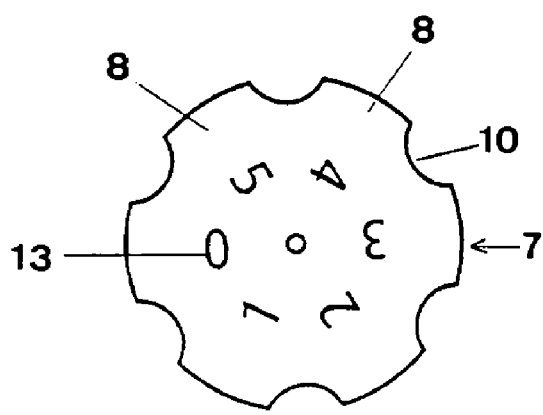
FIG. 4 shows a front view of the rotatable dish.

The dose setting element 5 comprises a disc 7 with a plurality of projections 8, 8' projecting from the disc 7. The dish 7 is located within the boundaries of the housing 1, and at least one of the projections 8 projects outside the boundaries of the housing 1 through a slot 9 provided in the side surface of the housing 1 as best seen in FIG. 3.

The dish 7 preferably has the shape of a thumb wheel with a number of notches or recesses 10 and a number of projections 8, 8' alternately located on the periphery of the disc 7. The projections 8, 8' need only be provided on a part of the circular periphery of the disc 7 depending on the number of doses which should be available in the specific injection device. The injection device could even have the possibility of setting only one volumetric dose size in which case only one projection 8 is needed.

The slot 9 has a longitudinal appearance with a length substantially longer than the width. The upper surface 11 of the slot 9 and the lower surface 12 forms the limits between which the projection 8 is exposed outside the boundaries of the housing 1.

When setting a dose, the user rotates the disc 7 in the clockwise direction by pressing the exposed projection 8 in the distal direction. The shown injection device is such designed that once the top surface of the projection 8 i.e. the surface defining the boundary between the projection 8 and the recess 10, aligns with the lower surface 12 of the slot 9 one full dose unit has been set. At the same time, the following projection 8' will have moved to a position which exposes this next projection 8'. By only having one projection 8 fully exposed at the time, the user can count the number of projections 8, 8' activated and are thereby given tactile information on the number of doses being set.

All though it is preferred to have one projection 8, 8' dedicated one dose setting unit, the dish 7 can have more or less projections 8, 8' for each volumetric dose unit if so wanted.

The dish 7 is provided with a scale bearing scale markings 13 indicating the number of dose units being set. When the dish 7 is concealed inside the boundaries of the housing 1, these scale markings 13 are only visible one scale marking 13 at the time through a window 14 provided in the housing 1. The window 14 could either be an opening in the housing 1 or it could be a transparent area.

FIGS. 5 and 6 discloses an alternative embodiment. The scale bearing the scale markings 23 is here provided on a non-rotatable part of the housing 21 and the window 24 through which the scale markings 23 can be inspected is provided in the disc 27 having projections 28. One surface or the predominant part of one surface of the dish 27 is visible through a large opening 20 in the front of the housing 1. The dish 27 can either be semi-transparent as shown in FIG. 5 such that the scale markings 23 outside the window 24 can be viewed when setting the dose or the dish 27 can be entirely coloured such that only the scale marking 23 relating to the set dose visible in the window 24 can be viewed.

When the thumb wheel like dish 27 is rotated, the window 24 will be moved in a circular direction in the opening 20 in the housing 21 into a position where the next scale marking 23 will be visible in the window 24.

As can be seen in FIG. 5, an extra slot 19' located opposite the slot 19 can be provided making the injection device equally suitable for both left-handed and right-handed persons.

Figures 7, 8:
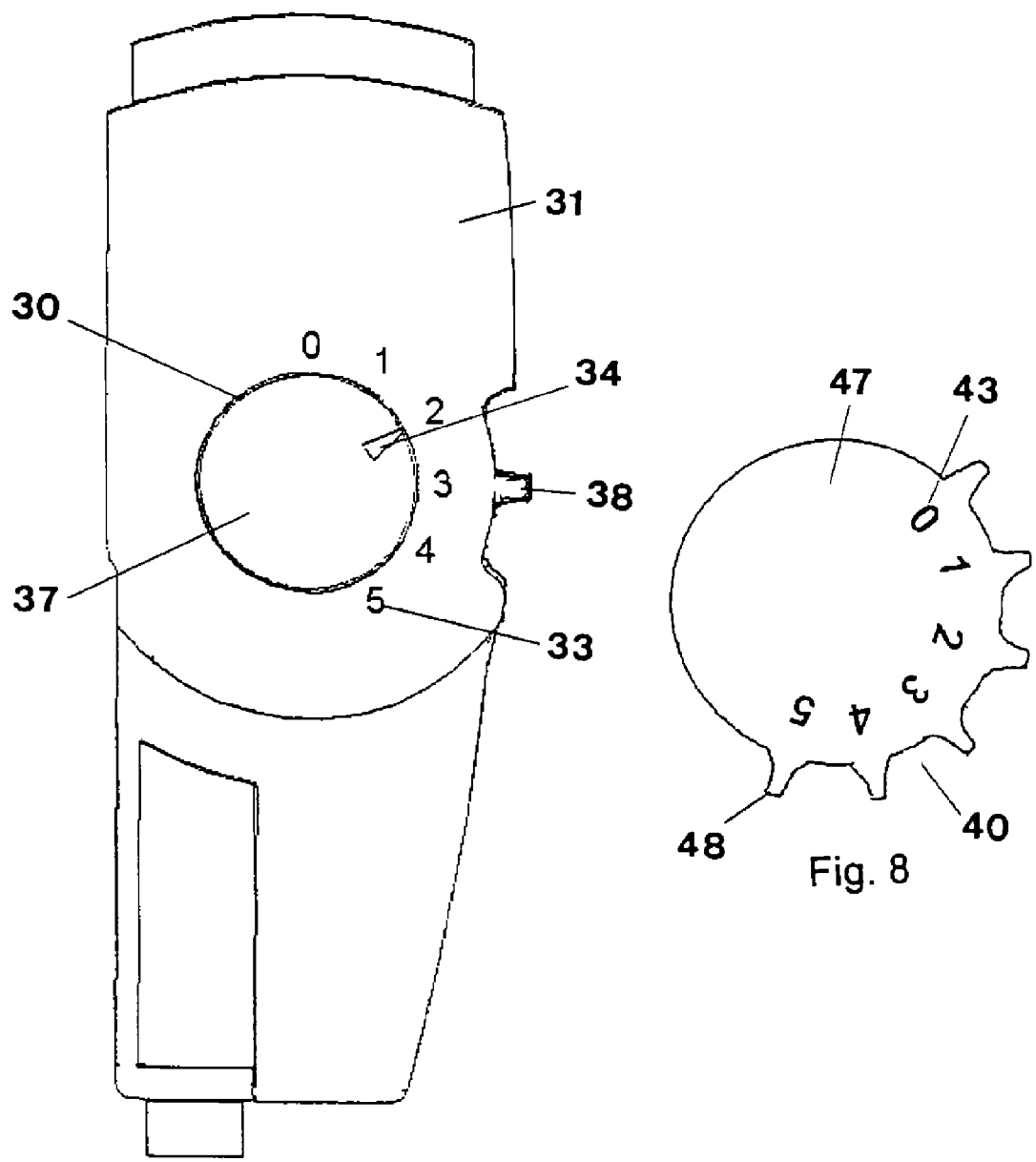
FIG. 7 shows a front view of an embodiment of the injection device according to the invention.
FIG. 8 shows a front view of the rotatable disc according to an embodiment of the invention.

A third embodiment is disclosed in FIG. 7. Here the scale markings 33 are provided on the housing 31, and a pointer 34 pointing out the set dose is provided on the rotatable dish 37, which dish 37 is visible through a large opening 30 in the front of the housing 31.

In this embodiment the projection 38 is somewhat narrower and sharper than shown in the previous embodiments, which can also be viewed in FIG. 8. As can also be seen in the embodiment shown in FIG. 8, the projections 48 need only be provided on a part of the circular periphery of the disc 47 depending on the number of doses which should be available in the specific injection device. The dish 47 is in this embodiment provided with five recesses 40 which is adequate for five different dose settings. The scale markings 43 is in this embodiment printed on the rotatable dish 47 in which case a pointer or a window most be provided on the housing.

Figure 9:
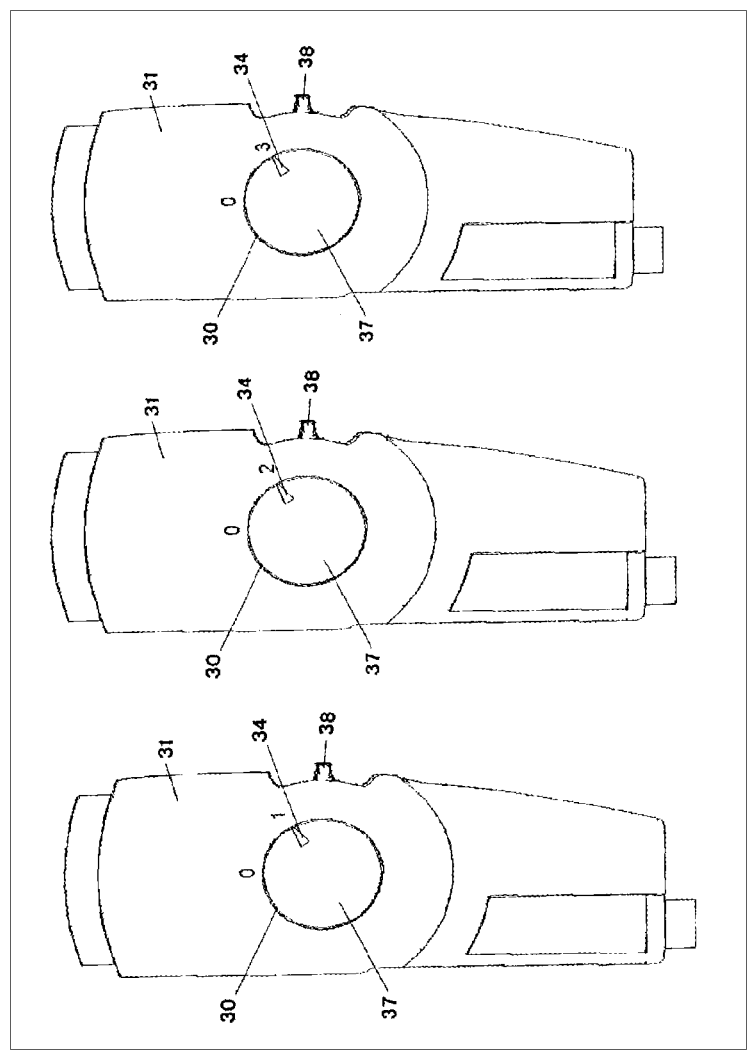
FIG. 9 shows a system according to an embodiment of the invention.

FIG. 9 discloses an alternative embodiment depicting a system comprising a plurality of substantially identical injection devices having different dose sizes, as shown by the different dose by pointer 34 in each device of the system.

In addition to the injection device, the invention also relates to a method of using the injection device for the administration of a fluid pharmaceutical formulation comprising a GLP-1 compound or a GLP-2 compound to a patient.

As disclosed in FIG. 1-4, first the pen needle 3 is connected to the injection device. The pen needle 3 can be any type of pen needle 3 known in the art, typically it will be a double-ended needle, 28G or smaller diameter, fixed in a hub provided with means for connecting the hub to the injection device. These means are typically a thread connection or some kind of a click-on mechanism.

Once the pen needle 3 is secured to the injection device, one of the up to five available dose sizes are set by rotating the dose setting element 5 the angular rotation needed in order to obtain the desired dose size. The dose size chosen will often relate to the body mass of the particular patient, such that patients with a low body mass would usually need one of the lower dose sizes while patients with a high body mass would require one of the larger dose sizes.

The pen needle 3 is then inserted into a suitable location on the body of the patient such that the sharp end of the pen needle penetrates the skin, and the selected dose are injected by pushing back the injection button 6 to its initial position.

After waiting a few seconds for the medicament to flow into the body, the pen needle 3 is retracted and the injection is complete.

Some preferred embodiments have been shown in the foregoing, but it should be stressed that the invention is not limited to these, but may be embodied in other ways within the subject matter defined in the following claims. Although the claims specifically relates to an injection device having up to five different dose sizes it is obvious that an injection device having two, up to three or up to four different dose sizes is also included in the claim scope. Since the general concept of the invention is to make an injection device with only a few different dose sizes to choose between, it is obvious that an injection device with more than five different settings but still with significantly fewer settings than the already known devices, such as up to six, up to seven or even up to eight different dose settings is also within the scope of the present invention.

CITED DOCUMENTS

The following documents are hereby incorporated by reference.

WO 96/29342
WO 96/32414
WO 97/31943
WO 97/39031
WO 98/03547
WO 98/08871
WO 98/08872
WO 98/10813
WO 99/43706
WO 00/09666
WO 01/83008
WO 02/30495
U.S. Pat. No. 5,424,286
U.S. Pat. No. 6,074,372

The invention claimed is:

1. A system of injection devices, comprising:
a plurality of substantially identical injection devices,
each individual injection device comprising a housing accommodating an ampoule containing medicine sufficient for a number of injections and a dose setting mechanism including a dose setting element with at least one projection by which a predetermined dose size can be selected,
wherein each of the plurality of injection devices has a different dose size, and
wherein the predetermined dose size may be selected by rotating the dose setting element mechanism relative to the housing, wherein the dose setting element is substantially located within the boundaries of the housing and reachable through an opening in the housing such that only one full projection is accessible outside the boundaries of the housing at a time.

2. A system of injection devices according to claim 1, wherein the medicine contained in the ampoule is a fluid pharmaceutical formulation comprising a GLP-1 compound.

3. A system of injection devices according to claim 2, wherein the GLP-1 compound comprises a lipophilic substituent which is attached, optionally via a spacer, to the epsilon amino group of a lysine residue.

4. A system of injection devices according to claim 3, wherein the lipophilic substituent has from 8 to 40 carbon atoms.

5. A system of injection devices according to claim 4, wherein the lipophilic substituent has from 12 to 24 carbon atoms.

6. A system of injection devices according to claim 4, wherein the lipophilic substituent has from 14 to 18 carbon atoms.

7. A system of injection devices according to claim 1, wherein the plurality of devices comprises up to five injection devices.

8. A system of injection devices according to claim 1, wherein each different predetermined dose size is volumetric determined.

9. A system of injection devices according to claim 1, wherein each different predetermined dose size is concentrational determined.

10. A system of injection devices according to claim 1, wherein the medicine contained in the ampoule is a fluid GLP-1 compound or a fluid GLP-2 compound.

11. A system of injection devices according to claim 1, wherein the projection extending outside the boundaries of the housing through the opening such that the dose setting element can be rotated by moving the exposed projection.

12. A system of injection devices according to claim 1, wherein the rotational axis of the dose setting mechanism is perpendicular to the longitudinal axis of the ampoule.

13. A system of injection devices according to claim 1, wherein the distance between two successive projections of the dose setting mechanism equals the setting of one dose unit.

14. A method of using an injection device according to claim 1 for the administration of a fluid pharmaceutical formulation comprising a GLP-1 compound or a GLP-2 compound to a patient, said method comprising:

selecting the injection device from the plurality of injection devices having the predetermined dose size which accommodates the individual patient, connecting a pen needle to the selected injection device, selecting the predetermined dose size, inserting the pen needle into the patient and injecting the predetermined dose of the fluid pharmaceutical formulation comprising a GLP-1 or a GLP-2 compound, and removing the pen needle from the patient after completing the injection of the predetermined dose size.

* * * * *